United States Patent [19]

Most et al.

[11] Patent Number: 4,661,614

[45] Date of Patent: Apr. 28, 1987

[54] PROCESS FOR THE PREPARATION OF IMINODIACETONITRILE

[75] Inventors: James T. Most, St. Louis; Thomas J. Richard, University City, both of Mo.

[73] Assignee: Monsanto Company, St. Louis, Mo.

[21] Appl. No.: 836,926

[22] Filed: Mar. 6, 1986

[51] Int. Cl.$^4$ ............................................ C07C 120/00
[52] U.S. Cl. .................................................... 558/346
[58] Field of Search ......................................... 558/346

[56] References Cited

U.S. PATENT DOCUMENTS 2,794,044  5/1957  Miller ................................. 558/346
3,904,668  9/1975  Gaudette et al. ................... 558/347

Primary Examiner—Joseph Paul Brust
Attorney, Agent, or Firm—Frank D. Shearin

[57] ABSTRACT

A process for preparing iminodiacetonitrile which comprises bringing together under reaction conditions formaldehyde, hydrogen cyanide and a source of ammonia under substantially stoichiometric conditions at a temperature between about 30° and about 65° C. at a pH between about 1.5 and about 5.5, preferably between about 3.5 and about 5.3, to produce the desired iminodiacetonitrile.

5 Claims, No Drawings

PROCESS FOR THE PREPARATION OF IMINODIACETONITRILE

BACKGROUND OF THE INVENTION

This invention relates to a process for preparing iminodiacetonitrile by the reaction of formaldehyde, hydrogen cyanide and an ammonia source.

The compound iminodiacetonitrile is a valuable chemical intermediate which is used to prepare iminodiacetic acid or its alkali metal salt, which is also a valuable chemical intermediate that is commercially available and useful for the preparation of a number of chemical compounds, such as the preparation of herbicides, pesticides, chelating agents, and detergent builders.

The prior art discloses a number of processes for the preparation of iminodiacetonitrile. For example, U.S. Pat. No. 3,904,668, to Gaudette et al, discloses that iminodiacetonitrile can be prepared by forming an aqueous mixture of hexamethylenetetramine, HCN, and glycolonitrile, and passing the mixture through a tubular reactor at about 100°–200° C. to form iminodiacetonitrile.

The prior art process that is most generally used for the preparation of iminodiacetonitrile has been that described by U.S. Pat. No. 2,794,044 to Miller, who stated that the obvious equation for the reaction producing iminodiacetonitrile is to react stoichiometric quantities of ammonia, formaldehyde and HCN. When, however, the reactants are mixed in the stoichiometric ratio demanded by the equation, no product can be isolated, regardless of the pH adjustment.

Despite these teachings in the prior art, it has now been found that iminodiacetonitrile can be produced in high yield under modest reaction conditions, contrary to the teachings of the prior art.

SUMMARY OF THE INVENTION

These and other advantages are achieved by a process for preparing iminodiacetonitrile which comprises: bringing together in a reaction zone formaldehyde, hydrogen cyanide, and a source of ammonia;

A. the mole ratio of formaldehyde to hydrogen cyanide being about 0.8 to 1.2,

B. the mole ration of ammonia to hydrogen cyanide being about 0.4 to 0.6,

C. at a pH between about 1.5 and about 5.5,

D. at a temperature between about 30° C. and about 65° C.,

DETAILED DESCRIPTION OF THE INVENTION

The reactants used in the present process are readily available, both on a laboratory scale and commercially. The formaldehyde can either be an aqueous solution or a paraformaldehyde product, but an aqueous solution of formaldehyde is preferred, since water should be present in the reaction zone. Hydrogen cyanide is also readily available. The source of ammonia can either be ammonia gas or an ammonium salt. It is evident to anyone skilled in the art that the amount of ammonia and/or ammonium ion in aqueous solution is governed by the known dissociation constant of ammonium ion.

The temperature of the reaction zone should be maintained somewhere between about 30° C. and about 65° C. At temperatures above about 65° C., the formation of undesirable byproducts is favored. At temperatures below about 30° C, undesirably long times are required to achieve satisfactory yields of iminodiacetonitrile. A temperature between about 40° C. and about 55° C. is preferred.

The pH of the aqueous reaction zone is critical. At a pH above about 5.5 the formation of undesirable byproducts, such as glycolonitrile and methylenebisiminodiacetonitrile is favored. It is preferred to maintain the pH between about 1.5 and 5.5, and even more preferred to maintain the pH between about 3.5 and about 5.3. At a pH below about 3, yields may be low, and at a pH above about 5.3, the formation of undesirable side products is favored.

The ammonia source is important with respect to the pH. As noted above, the pH of the aqueous reaction zone should be maintained between about 1.5 and about 5.5, more preferably between about 3.5 and about 5.3. For example, if ammonia gas or ammonium hydroxide is used, it is necessary to add simultaneously a strong acid, such as hydrochloric acid or sulfuric acid, to the reaction zone to adjust the pH to the desired level. If, however, ammonium sulfate is used as a source of ammonia, it may be necessary to add simultaneously a source of base, such as sodium hydroxide, potassium hydroxide, and the like, to adjust the pH to the desired level in the reaction zone.

There are a number of sources of ammonia that can be used in the process of the present invention. For example, ammonia gas can be used. Other sources include ammonium hydroxide, ammonium acetate, ammonium sulfate, ammonium nitrate, ammonium chloride, and the like. It is only necessary that the pH of the aqueous reaction zone be maintained between the desired pH levels, and this can be accomplished by means known to those skilled in the art.

It is also important in the process of the present invention that the reactants are brought together in the reaction zone in substantially stoichiometric amounts of favor the production of the desired iminodiacetonitrile. The addition of the reactants to the reaction zone separately favors the formation of undesired byproducts, such as glycolonitrile or hexamethylenetetramine or other products. The simultaneous addition of the reactants under the desired pH conditions favors the formation of the iminodiacetonitrile over the other undesired byproducts, such as glycolonitrile, and methylene-bis-iminodiacetonitrile.

The iminodiacetonitrile can be recovered by any number of techniques known to those skilled in the art, for example by evaporation and crystallization, filtration, centrifugation and the like. On the other hand, the iminodiacetonitrile can be hydrolyzed to iminodiacetic acid or its salts by well known reactions, with or without separation of the iminodiacetonitrile, and the desired product recovered by conventional techniques.

This invention is further illustrated by, but not limited to, the following examples.

EXAMPLE 1

To a one-liter baffled Ace reactor, equipped with a five-necked flask head, was placed a mechanical stirrer, thermocouple, temperature controller, condenser, subsurface drain tube, external steam and cold water delivery system for heating and cooling, a pH controller and level sensor, was continuously flowed ammonium nitrate solution (4.9445 grams/minute, 60%, 0.037 mole per minute), hydrogen cyanide (2.007 grams per minute, 0.074 mole/min.) and formaldehyde (6.2583 gram/min, 35.56% 0.74 mole/min). This agitated mixture was then controlled at a pH of 5.1 by the controlled addition of sodium hydroxide solution (50%) and heated to 47° C. until initiation of the reaction (approximately 10 minutes). After about 40 minutes, the level (or residence time) was set in the reactor, and the solution was continuously pumped into a second stage reactor, which was identical to the first reactor. The incoming stream was heated to approximately 65° C. and controlled at a pH of 5.1 with the addition of 50% sodium hydroxide solution. After about 40 minutes, the level was set in the reactor, causing iminodiacetonitrile to be continuously pumped out and collected. The above described stream was maintained for approximately 190 minutes. After this period, all flows were stopped, the second vessel was drained into the main collection vessel, and the first reactor was drained into a separate bottle and weighed. Samples of the second-stage reactor were taken at regular intervals during the run by means of a six-port sampling valve and analyzed. Analysis included an analysis for iminodiacetonitrile, methylene-bis-diacetonitrile, aminoacetonitrile, glycolonitrile, hydrogen cyanide and other impurities. The iminodiacetonitrile yield was 49.3%.

EXAMPLE 2

The same procedure as used in Example 1 was used except that ammonium acetate was used. With a flow rate of ammonium acetate (5.711 g/minute, 50%, 0.037 mole/min), HCN (2 g/min, 0.074 mole/min) and $CH_2O$ (6.187 g/min, 35.95%, 0.074 mole/min), the iminodiacetonitrile yield for the reaction was 53.4%.

EXAMPLE 3

The reactor system was the same as that used in Example 1. Ammonium acetate (5.717 g/min, 50%, 0.037 mole/min), hydrogen cyanide (2.00 g/min, 0.074 mole/min) and formaldehyde (6.11 gram/min, 36.40%, 0.074 mole/min) was added. This agitated mixture was then controlled at a pH of 5.1 by the controlled addition of sodium hydroxide (50% aqueous solution) and heated to 47° C. until initiation of the reaction after about 10 minutes. After approximately 83 minutes after the reaction was initiated, the level (or residence time) was set in the reactor and the solution was continuously pumped into a collection vessel. The above described scheme was maintained for 140 minutes. After this period, all flows were stopped and the reactor immediately drained into collection vessels and weighed. Samples of the reaction mixture were taken at regular intervals during the run by a six-port sampling valve and analyzed for iminodiacetonitrile methylene-bis-iminodiacetonitrile, and the like. The iminodiacetonitrile yield was 61.9%.

EXAMPLE 4

The apparatus used was the same as that in Example 1. To the reactor was continuously flowed ammonium acetate (5.71 grams/minute, 50%, 0.037 mole/minute), hydrogen cyanide (2.00 gram/minute, 0.074 mole/minute), and formaldehyde (6.174 g/minute, 36.03% 0.074 mole/min) for 40 minutes. The pH was controlled at 3.5 by the addition of 50% sodium hydroxide solution. After all the reagents were added, the mixture was maintained under agitation and appropriate temperature and pH control for another 80 minutes. The reaction mixture was then sampled for the various products. The iminodiacetonitrile for the reaction was approximately 74.2%.

Although the invention has been described in terms of specified embodiments which are set forth in considerable detail, it should be understood that this is by way of illustration only, and that alternative embodiments and operating techniques will become apparent to those skilled in the art in view of the disclosure. Accordingly, modifications can be made without departing from the spirit of the described invention.

We claim:

1. A process for preparing iminodiacetonitrile which comprises bringing together simultaneously under reaction conditions formaldehyde, hydrogen cyanide and a source of ammonia,
   a. the mole ratio of formaldehyde to hydrogen cyanide being about 0.8 to 1.2,
   b. the mole ratio of ammonia to hydrogen cyanide being about 0.4 to 0.6,
   c. at a pH between about 1.5 and about 5.3,
   d. at a temperature between about 30° C. and about 65° C.

2. A process as set forth in claim 1 wherein the formaldehyde, hydrogen cyanide and the source of ammonia are brought together in substantially stoichiometric amounts.

3. A process of claim 1 wherein the pH is maintained between about 3.5 and about 5.3.

4. A process of claim 1 wherein the temperature is maintained between about 40° C. and about 55° C.

5. A process of claim 3 wherein the ammonia source is an ammonium salt.

* * * * *